United States Patent
Natsume et al.

(10) Patent No.: US 10,695,317 B2
(45) Date of Patent: Jun. 30, 2020

(54) COMPOSITION FOR PROMOTING PRODUCTION OF BRAIN-DERIVED NEUROTROPHIC FACTOR

(71) Applicant: Meiji Co., Ltd., Tokyo (JP)

(72) Inventors: Midori Natsume, Odawara (JP); Yukio Ohshiba, Odawara (JP); Taketo Yamaji, Odawara (JP); Hiroyuki Ito, Odawara (JP); Toshihiko Osawa, Nagoya (JP)

(73) Assignee: Meiji Co., Ltd. (JP)

( * ) Notice: Subject to any disclaimer, the term of this patent is extended or adjusted under 35 U.S.C. 154(b) by 0 days.

(21) Appl. No.: 15/572,189

(22) PCT Filed: May 10, 2016

(86) PCT No.: PCT/JP2016/063797
§ 371 (c)(1),
(2) Date: Nov. 7, 2017

(87) PCT Pub. No.: WO2016/181945
PCT Pub. Date: Nov. 17, 2016

(65) Prior Publication Data
US 2018/0117001 A1   May 3, 2018

(30) Foreign Application Priority Data

May 11, 2015   (JP) .................. 2015-096205

(51) Int. Cl.
*A61K 31/353* (2006.01)
*A61K 36/185* (2006.01)
*A61P 25/24* (2006.01)

(52) U.S. Cl.
CPC .......... *A61K 31/353* (2013.01); *A61K 36/185* (2013.01); *A61P 25/24* (2018.01)

(58) Field of Classification Search
CPC ...... A61K 31/353; A61K 36/185; A61P 25/24
See application file for complete search history.

(56) References Cited

U.S. PATENT DOCUMENTS 8,575,368 B2   11/2013   Nagamine

FOREIGN PATENT DOCUMENTS

| CN | 102317468 A | 1/2012 |
|---|---|---|
| JP | 4380991 B2 | 12/2009 |
| JP | 2010530246 A | 9/2010 |
| JP | 2012517970 A | 8/2012 |
| WO | 02076381 A2 | 10/2002 |
| WO | 2008157039 A1 | 12/2008 |
| WO | 2010091981 A2 | 8/2010 |
| WO | 2014144972 A1 | 9/2014 |

OTHER PUBLICATIONS

3 Healthy Reasons to Enjoy Chocolate Every Day; www.mindbodygreen.com/0/9854/3-healthy-reasons-to-enjoy-chocolate-every-day.html; retrieved from the web May 8, 2018 (Year: 2013).*
Thozhukat Sathyapalan, Stephen Beckett, Alan S Rigby, Duane D Mellor, Stephen L Atkin, High cocoa polyphenol rich chocolate may reduce the burden of the symptoms in chronic fatigue syndrome, Nutrition Journal 2010, 9:55 (Year: 2010).*
Bisson et al., Effects of long-term administration of a cocoa polyphenolic extract (Acticoa powder) on cognitive performances in aged rats, British Journal of Nutrition, 2008, pp. 94-101, vol. 100, No. 1.
Cimini et al., Cocoa Powder Triggers Neuroprotective and Preventive Effects in a Human Alzheimer's Disease Model by Modulating BDNF Signaling Pathway, Journal of Cellular Biochemistry, 2013, pp. 2209-2220.
Hou et al., Anti-depressant natural flavonols modulate BDNF and beta amyloid in neurons and hippocampus of double TgAD mice, Neuropharmacology, 2010, pp. 911-920, vol. 58.
Kitaura et al., Abstracts of the Annual Meeting of the Pharmaceutical Society of Japan, 2005, pp. 132, vol. 125, No. 4 (cited in the International Search Report for PCT/JP2016/063797).
Natsume, Functional Food, Medical Online, 2011, pp. 374-378, vol. 4, No. 4 (English-language Abstract).
Shimizu et al., Deodorizing Effect of Cacao Polyphenols against Methyl Mercaptan, Nippon Shokuhin Kagaku Kogak Kaishi, 2001, pp. 238-245, vol. 48, No. 4 (English-language Abstract).
Stringer et al., Plant-derived flavanol (−)epicatechin mitigates anxiety in association with elevated hippocampal monoamine and BDNF levels, but does not influence pattern separation in mice, Translational Psychiatry, 2015, pp. 1-9, vol. 5.
Tian et al., Intrathecal Epigallocatechin Gallate Treatment Improves Functional Recovery After Spinal Cord Injury by Upregulating the Expression of BDNF and GDNF, Neurochem Res., 2013, pp. 772-779, vol. 38.
Yoshimura et al., Blood Levels of Brain-derived Neurotrophic Factor (BDNF) in Major Depressive Disorder, 2010, pp. 982-985 (English-language Abstract).
Boosting Brain Power—With Chocolate; https://www.sciencedaily.com/releases/2007/02/070221101326.htm; Feb. 22, 2007.
Gundimeda, "Green tea catechins potentiate the neuritogenic action of brian-derived neurotrophic factor: Role of 67-kDa laminin receptor and hydrogen peroxide," Biochemical and Biophysical Research Communications, 2014, pp. 218-224, vol. 445.

(Continued)

*Primary Examiner* — Sarah Pihonak
*Assistant Examiner* — Jason Deck
(74) *Attorney, Agent, or Firm* — The Webb Law Firm

(57) ABSTRACT

An object of the present invention is to provide novel composition and agent for promoting the production of a brain-derived neurotrophic factor (BDNF) and a novel method for promoting the production of BDNF. The present invention provides a composition for promoting the production of BDNF and an agent for promoting the production of BDNF, each comprising cacao polyphenols. The present invention also provides a method for promoting the production of BDNF, comprising feeding cacao polyphenols in a daily intake which is effective in promoting the production of BDNF for at least 2 weeks.

15 Claims, No Drawings

(56) References Cited

OTHER PUBLICATIONS

Mastroiacovo, "Cocoa flavanol consumption improves cognitive function, blood pressure control, and metabolic profile in elderly subjects: the Cocoa Cognition, and Aging (CoCoA) Study—a randomized controlled trial 1-4," Am J Clin Nutr, 2015, pp. 538-548, vol. 101.

Williams, "Blueberry-induced changes in spatial working memory correlate with changes in hippocampal CREB phosphorylation and brain-derived neurotrophic factor (BDNF) levels," Free Radical Biology & Medicine, 2008, pp. 295-305, vol. 45.

* cited by examiner

COMPOSITION FOR PROMOTING PRODUCTION OF BRAIN-DERIVED NEUROTROPHIC FACTOR

CROSS-REFERENCE TO RELATED APPLICATIONS

This application is the U.S. National Phase of International Application No. PCT/JP2016/063797 filed May 10, 2016, and claims priority to Japanese Patent Application No. 2015-096205 filed May 11, 2015, the disclosures of which are hereby incorporated in their entirety by reference.

TECHNICAL FIELD

The present invention relates to a composition for promoting the production of a brain-derived neurotrophic factor, and, more specifically, relates to a composition comprising cacao polyphenols for promoting the production of a brain-derived neurotrophic factor.

BACKGROUND ART

A brain-derived neurotrophic factor (sometimes referred to as "BDNF protein" or merely as "BDNF" herein) is a secretory protein which is known as one of neurotrophic factor families. The secreted BDNF protein is known to bind to receptor tyrosine kinase, TrkB receptor and to be involved in neurogenesis and neural development. Recently, it has been reported that, in patients suffering from depression, the BDNF protein concentration in serum decreases, but that the decreased concentration recovers when an antidepressant takes effect (Non-Patent Document 1). Hence, the substance acting on this factor is expected to successfully improve disease states such as depression.

Plant polyphenols contained in various fruits and vegetables, among others, cacao polyphenols are known to have various physiological activities. For example, it has hitherto been known that procyanidin is a potent inhibitor of amyloid and α-synuclein/NAC fibrillation (Patent Document 1) and that N-phenylpropenoyl amino acid amide suppresses the aggregation of amyloid β-peptides (Patent Document 2). However, none of the documents disclose the involvement of cacao polyphenols in the expression and secretion of BDNF.

REFERENCE LIST

Patent Documents
Patent Document 1: JP 4380991 B
Patent Document 2: JP 2012-517970 T
Non-Patent Document
Non-Patent Document 1: Psychiatria et Neurologia Japonica, 112 (10): 982-985, 2010

SUMMARY OF INVENTION

An object of the present invention is to provide a novel composition for promoting the production of BDNF and a novel agent for promoting the production of BDNF.

The present inventors have found that a fat-processed composition comprising a high concentration of cacao polyphenols significantly increase the BDNF protein concentration in human serum (especially, BDNF protein concentration in serum of a human having a low initial value of the BDNF protein concentration in serum). The present invention is based on these findings.

The present invention provides the following inventions.

[1] A composition for promoting the production of a brain-derived neurotrophic factor (BDNF) and an agent for promoting the production of BDNF, each comprising cacao polyphenols.

[2] The composition for promoting the production of BDNF and agent for promoting the production of BDNF according to [1], wherein the cacao polyphenols comprise 8% by mass or more of monomeric to tetrameric polyphenols.

[3] The composition for promoting the production of BDNF and agent for promoting the production of BDNF according to [1] or [2], which comprise a daily intake of the cacao polyphenols which is effective in promoting the production of BDNF.

[4] The composition for promoting the production of BDNF and agent for promoting the production of BDNF according to [3], which are packaged in each effective daily intake.

[5] The composition for promoting the production of BDNF and agent for promoting the production of BDNF according to [3] or [4], wherein the daily intake which is effective in promoting the production of BDNF ranges from 10 mg to 2,000 mg (total amount of polyphenols).

[6] The composition for promoting the production of BDNF and agent for promoting the production of BDNF according to any one of [1] to [5], which allow feeding of the cacao polyphenols for at least 2 weeks.

[6-1] The composition for promoting the production of BDNF and agent for promoting the production of BDNF for promoting the production of BDNF and agent for promoting the production of BDNF according to any one of [1] to [6], which allow feeding of the cacao polyphenols in a daily amount of 10 mg to 2,000 mg (total amount of polyphenols) for at least 2 weeks.

[7] The composition for promoting the production of BDNF and agent for promoting the production of BDNF according to any one of [1] to [6] and [6-1], which are in the form of a fat-processed composition.

[8] A method for promoting the production of BDNF comprising feeding cacao polyphenols in a daily intake which is effective in promoting the production of BDNF for at least 2 weeks.

[9] The method for promoting the production of BDNF according to [8], wherein the daily intake which is effective in promoting the production of BDNF ranges from 10 mg to 2,000 mg (total amount of polyphenols).

[10] The method for promoting the production of BDNF according to [8] or [9], wherein the cacao polyphenols are fed in the form of a fat-processed composition.

[11] Use of cacao polyphenols for the manufacture of a composition for promoting the production of BDNF or an agent for promoting the production of BDNF.

[12] A composition or agent for treating, preventing or improving a disease and a symptom which are effectively treated, prevented or improved by promoting the production of BDNF, which comprises cacao polyphenols.

[13] A method for treating, preventing or improving a disease and a symptom which are effectively treated, prevented or improved by promoting the production of BDNF, which comprises administering an effective amount of cacao polyphenols to a subject.

[14] Use of cacao polyphenols for the manufacture of a composition for treating, preventing or improving a disease and a symptom which are effectively treated, prevented or improved by promoting the production of BDNF, or an agent for treating, preventing or improving the disease and symptom.

Since the agent for promoting the production of BDNF and composition for promoting the production of BDNF according to the present invention utilize polyphenols contained in cacao which has been used as a raw material for foods for a long time, the agent and composition according to the present invention are advantageous in that they have less side effects and high safety even when taken for a long term.

DETAILED DESCRIPTION OF THE INVENTION

The "cacao polyphenols" used in the present invention means polyphenols contained in cacao, i.e., cacao-derived polyphenols. Thus, cacao polyphenols, which are extracted (including crude extraction) or purified (including crude purification) from plant bodies of cacao or processed products thereof, can typically be used as the active ingredient of the present invention, but polyphenols prepared by a chemical synthesis method may be used partially or wholly as the cacao polyphenols. Examples of the cacao polyphenols include monomers such as catechin, epicatechin and clovamide and oligomers (dimers and higher oligomers) such as tannin and procyanidin obtained by polymerization of catechin or the like.

In the present invention, examples of the plant bodies of cacao or processed products thereof which can serve as raw materials for cacao polyphenols can include various sites of the plant bodies or various cacao bean-processed products such as cacao bark, cacao leaves, cacao beans, cacao shell, cacao liquor, defatted cacao liquor and cocoa powder. Cacao liquor is obtained by grinding cacao beans, and defatted cacao liquor can be obtained by removing oil or fat from cacao liquor. The method for removing oil or fat is not particularly limited, and oil or fat can be removed by a known method such as compression. Cocoa powder would be obtained by crushing defatted cacao liquor. Also, when a plant body of cacao or a processed product thereof is used as a raw material for extraction, cacao liquor and cocoa powder subjected to pulverizing treatment such as grinding or crushing are preferably used, for example, from the viewpoint of extraction efficiency. It should be noted that any substances other than the plant body of cacao can be included in the plant body of cacao with or without intention. Also when the plant body of cacao or processed product thereof is used as a raw material for extraction, any substances other than the plant body of cacao can be included. Further, any substances other than the plant body of cacao can be included intentionally or unintentionally in the cacao liquor and cocoa powder.

An extraction method using a plant body of cacao or a processed product thereof as a raw material is known, and a cacao polyphenol-containing composition can be prepared according to the descriptions, for example, in JP 2009-183229 A and JP 2011-93807 A. An extraction solvent is not particularly limited, but water or an alcohol such as ethanol is preferably used. A purification method using a plant body of cacao or a processed product thereof as a raw material is not particularly limited, and known methods such as synthetic adsorbents, ion exchange resins, ultrafiltration and activated clay can be used as the purification method.

In the present invention, cacao polyphenols can comprise monomeric to tetrameric polyphenols in an amount of 8% by mass or more, preferably 8 to 50% by mass, more preferably 8 to 30% by mass, even more preferably 8 to 20% by mass, further preferably 8 to 15% by mass, especially preferably 8 to 12% by mass, most preferably 10 to 12% by mass or more, based on the total mass of the cacao polyphenols.

In the present invention, the polyphenol content can be measured by the Prussian blue method. For example, the polyphenol content can be calculated by using commercial epicatechin as a reference material, according to the method described in Martin L. Price and Larry G. Butler, J. Agric Food Chem., Vol. 25, No. 6, 1268-1273, 1977.

For effective administration or feeding of cacao polyphenols, a composition comprising concentrated cacao polyphenols is preferably used in the present invention, and, in this case, a cacao polyphenol-concentrated composition obtained according to a known method (for example, the method described in JP 2009-183229 A) can be used in the present invention.

Since cacao polyphenols can be prepared by using a plant body of cacao as a raw material, the composition for promoting the production of BDNF and agent for promoting the production of BDNF according to the present invention may comprise a cacao bean-derived ingredient other than cacao polyphenols. Examples of such an ingredient include theobromine, caffeine, amino acids, peptides and fatty acids. Also, the composition for promoting the production of BDNF and agent for promoting the production of BDNF according to the present invention may comprise an ingredient which is not derived from cacao beans.

The composition for promoting the production of BDNF and agent for promoting the production of BDNF according to the present invention may comprise N-phenylpropenoyl amino acid amide in an amount of 100 mg/kg or less, and can be compositions comprising N-phenylpropenoyl amino acid amide in an amount of preferably 80 mg/kg or less, more preferably 60 mg/kg or less, even more preferably 50 mg/kg or less, further preferably 25 mg/kg or less. N-phenylpropenoyl amino acid amide is contained in cacao plant bodies, and cacao beans are treated according to the method described in Sanbongi et al., J. Agric Food Chem., Vol. 46, 454-457 (1998), thereby making it possible to obtain cacao polyphenols in a concentration as described above. Also, the composition for promoting the production of BDNF and agent for promoting the production of BDNF according to the present invention are preferably prepared without using a raw material containing isothiocyanate, and, more preferably, can be compositions which are substantially free of isothiocyanate.

As will be indicated in the Example below, cacao polyphenols have the BDNF production promoting effect. Thus, cacao polyphenols can be used as an agent for promoting the production of BDNF, and can also be used in the method for promoting the production of BDNF. Also, cacao polyphenols can be used as the composition for promoting the production of BDNF.

Here, the phrase "promoting the production of a brain-derived neurotrophic factor (BDNF)" means promoting the expression and secretion of BDNF in nerve cells, and the degree of promoting the production of BDNF can be evaluated based on the BDNF protein concentration in serum as an index (see Example 1). Specifically, when the BDNF protein concentration in serum after feeding or administration of cacao polyphenols is beyond the BDNF protein concentration in serum before feeding or administration, preferably about 1.1 times or more, more preferably about 1.2 times or more, even more preferably about 1.3 times or more, further preferably 1.4 times or more, especially preferably 1.5 times or more, further especially preferably 1.6 times or more, further especially preferably 1.8 times or more, most preferably 2 times or more, the production of BDNF can be determined to have been promoted.

The method for promoting the production of BDNF according to the present invention can be carried out by feeding or administering an effective amount of cacao polyphenols to a human or non-human animal.

The use of cacao polyphenols in the present invention may be use thereof in a human and non-human animal and a sample derived therefrom, and both of therapeutic use and non-therapeutic use are intended. Here, the term "non-therapeutic" means exclusion of activities of operation on, treatment of, or diagnosis involving a human (i.e., medical activities to a human), and specifically means exclusion of a method for operation on, treatment of, or diagnosis involving a human by a doctor or a person who receives instructions from a doctor.

In the present invention, cacao polyphenols can be used in the treatment, prevention or improvement of a disease and a symptom which are effectively treated, prevented or improved by promoting the production of BDNF.

Examples of the disease and symptom which are effectively treated, prevented or improved by promoting the production of BDNF include mental·neurological diseases such as depression, depressive state, schizophrenia, developmental disorder and dementia. Cacao polyphenols can promote the production of BDNF as will be indicated in the Example below, and it has hitherto been indicated that the amount of BDNF to be expressed or secreted affects mental·neurological diseases such as depression, depressive state, schizophrenia and developmental disorder (for example, Chao, M. V., Rajagopal, R., & Lee, F. S. (2006) Clin. Sci. (Lond.), 110, 167-173). Accordingly, cacao polyphenols can be used as an agent for treating, preventing or improving mental·neurological diseases, and can also be used in methods for treating, preventing and improving mental·neurological diseases.

The composition for promoting the production of BDNF and agent for promoting the production of BDNF according to the present invention and the treating, preventing and improving agent according to the present invention can be provided in the form of medicaments, quasi-drugs, beverage and food products, feed or the like, and can be realized according to the following description. Also, the method for promoting the production of BDNF according to the present invention and the treating, preventing and improving methods according to the present invention can be carried out according to the following description.

Cacao polyphenols, which are the active ingredient of the present invention, can be orally administered to humans and non-human animals. Examples of the oral agent include granules, powders, tablets (including sugar-coated tablets), pills, capsules, syrups, emulsions and suspensions. These formulations can be formulated through the use of a pharmacologically acceptable carrier by a technique which is normally carried out in the art. Examples of the pharmacologically acceptable carrier include excipients, binders, diluents, additives, perfumes, buffers, thickeners, colorants, stabilizers, emulsifiers, dispersants, suspending agents and preservatives.

Cacao polyphenols, which are the active ingredient of the present invention, can also be administered into the body of a human or non-human animal by means other than oral administration including tube administration, nasal tube administration, intravenous drip and suppository, according to the form of the composition for promoting the production of BDNF and agent for promoting the production of BDNF according to the present invention. For example, a viscous liquid composition comprising cacao polyphenols or a semi-solid composition comprising cacao polyphenols can be administered also to humans and non-human animals with impaired masticating and swallowing functions so that oral feeding or oral administration cannot be carried out. The feeding or administration of the composition for promoting the production of BDNF and agent for promoting the production of BDNF according to the present invention, other than oral feeding, can be expected to treat, prevent and improve mental·neurological diseases such as depression, depressive state, schizophrenia and developmental disorder of these humans and non-human animals, even when their masticating and swallowing functions are impaired, for example, by aging.

Cacao polyphenols, which are the active ingredient of the present invention, can be orally fed to humans and non-human animals. In the case of oral feeding of cacao polyphenols, cacao-derived polyphenols may be either in an isolated, purified or roughly-purified form or in the form of a food comprising cacao polyphenols or a raw material for the food. When cacao polyphenols are orally fed to humans and non-human animals, its state can arbitrarily be selected from an ordinary-temperature state, a warm state, a cold state and the like.

When cacao polyphenols, which are the active ingredient of the present invention, are provided as a food, cacao polyphenols can be directly incorporated in the food. The food is a food comprising an effective amount of cacao polyphenols. The phrase "comprising an effective amount of" cacao polyphenols refers to a cacao polyphenol content to be taken within a range as will be described later, when a normally-eaten amount of individual foods is fed. The term "food," as used herein, includes health foods, functional foods, foods with health claims (for example, foods for specified health uses, foods with nutrient function claims, and foods labeled with functions) and foods for special dietary uses (for example, foods for infants, foods for expectant and nursing mothers, and foods for sick persons). The form of the "food" is not particularly limited, and may be a drink form, a semi-liquid or gel form or a solid form.

Cacao polyphenols have the BDNF production promoting effect, and thus can be provided in such a state that it is incorporated in foods taken daily and foods taken as supplements. The forms and shapes of the foods provided in the present invention are not particularly limited, but the foods are preferably foods composed of cacao beans as the main raw material, more preferably fat-processed compositions, even more preferably chocolate and cocoa.

A cacao polyphenol-concentrated composition can be used in the present invention for effective feeding of cacao polyphenols, as described above. Accordingly, foods and supplements comprising cacao beans as the raw material are, for example, preferably those comprising cacao polyphenols in a high concentration, more preferably fat-processed compositions comprising cacao polyphenols in a high concentration, even more preferably chocolate and cocoa comprising cacao polyphenols in a high concentration.

The cacao polyphenol content in the foods and supplements is not particularly limited so long as cacao polyphenols can be fed, but, from effective feeding of cacao polyphenols, the content thereof in the fat-processed composition can be defined as, for example, 1 to 10% by mass, preferably 1.2 to 8% by mass, more preferably 1.4 to 6% by mass, even more preferably 1.6 to 4% by mass, further preferably 1.8 to 3.5% by mass, especially preferably 2 to 3.4% by mass based on the solid content of the composition.

The foods which are provided in the present invention include foods comprising cacao beans as the main raw material, such as chocolate and cocoa, and, further, are not particularly limited so long as the foods can comprise cacao polyphenols. Examples of the foods include starch-based foods such as breads, biscuits, noodles, crackers and nutritional supplement bars; various confectionaries such as candies, gums, gummies and snacks; milk and dairy products such as cow milk, processed milk, ice cream, fermented milk (for example, yogurt), milk beverages, cheese, butter, and cream; desserts such as pudding, jellies, bavarois and mousse; beverages such as non-alcoholic beverages and alcoholic beverages; processed products made from livestock meat such as hams and sausages; processed products made from fish meat such as boiled fish paste (kamaboko), tubular roll of boiled fish paste (chikuwa) and fish meat sausages; fruit processed products such as jams and puree; and flavorings such as roux and sauce. Cacao polyphenols can appropriately be incorporated at a proper manufacturing process stage according to the properties and purposes of the respective foods.

The medicaments and foods according to the present invention utilize polyphenols contained in cacao beans which have been traditionally used importantly as foods, and thus can be used safely to mammals in need thereof (for example, humans, mice, rats, rabbits, dogs, cats, cows, horses, pigs, and monkeys). The amount of cacao polyphenols to be administered or fed can be determined depending, for example, on the sex, age and body weight of recipients, symptom, administration time, dosage form, administration route and drug to be used in combination. For example, in the case of oral administration of cacao polyphenols as a medicament, cacao polyphenols can be administered in a daily amount ranging from 10 to 2,000 mg, preferably from 50 to 1,800 mg, more preferably from 100 to 1,600 mg, even more preferably from 150 to 1500 mg, further preferably from 200 to 1,400 mg, especially preferably from 300 to 1,200 mg, further especially preferably from 400 to 1,100 mg, most preferably from 500 to 1,000 mg for adults. In the case of feeding of cacao polyphenols as a food, cacao polyphenols can be administered in a daily amount ranging from 10 to 2,000 mg, preferably from 50 to 1,800 mg, more preferably from 100 to 1,600 mg, even more preferably from 150 to 1,500 mg, further preferably from 200 to 1,400 mg, especially preferably from 300 to 1,200 mg, further especially preferably from 400 to 1,100 mg, most preferably from 500 to 1,000 mg for adults.

As will be indicated in the Example below, it was confirmed that the serum BDNF protein concentration significantly increased, upon intake of cacao polyphenols, in subjects (humans and non-human animals) having a low initial value of the serum BDNF protein concentration. From the fact that the subjects having a low initial value of the serum BDNF protein concentration showed a higher degree of increase than those of all the subjects, it was suggested that this increasing effect was more effective on the subjects having a low initial value. Hence, according to a preferred embodiment of the present invention, the composition for promoting the production of BDNF and agent for promoting the production of BDNF according to the present invention and the treating, preventing and improving agents according to the present invention can be administered or fed to humans and non-human animals having a low initial value of the serum BDNF protein concentration. Also, according to a preferred embodiment of the present invention, the method for promoting the production of BDNF according to the present invention and the treating, preventing and improving methods according to the present invention can be carried out for humans and non-human animals having a low initial value of the serum BDNF protein concentration. The "humans and non-human animals having a low initial value of the serum BDNF protein concentration" referred to herein have a serum BDNF concentration before feeding (Day 0) ranging from 0.1 to 6 ng/ml, preferably from 0.1 to 5.5 ng/ml, more preferably from 0.1 to 5 ng/ml, even more preferably from 0.1 to 4.5 ng/ml, further preferably from 0.1 to 4 ng/ml, especially preferably from 0.1 to 3 ng/ml, further especially preferably from 0.1 to 2.5 ng/ml, most preferably from 0.1 to 2 ng/ml.

The composition for promoting the production of BDNF and agent for promoting the production of BDNF according to the present invention are used, without limitation, in combination with any other composition which can be orally fed. For example, they are used in combination with a material or composition which can be expected to prevent, treat and improve mental·neurological diseases such as depression, depressive state, schizophrenia and developmental disorder, thereby making it possible to further enhance the BDNF production promoting effect.

The composition for promoting the production of BDNF and agent for promoting the production of BDNF according to the present invention can be provided as a composition comprising a daily intake of cacao polyphenols which is effective in promoting the production of BDNF. In this case, the composition for promoting the production of BDNF and agent for promoting the production of BDNF may be packaged so that an effective daily intake thereof can be taken, and the packaging form may be either single package or multiple package so long as the effective daily intake thereof can be taken. When the composition and agent are provided in a packaged form, it is desirable to indicate the intake on a package so as to ensure taking of the effective daily intake, or to provide a document which indicates the intake together. When the effective daily intake is provided in multiple package, a plurality of packages for the effective daily intake can also be provided as a set, for convenient feeding.

The packaging form for providing the composition for promoting the production of BDNF and agent for promoting the production of BDNF according to the present invention is not particularly limited so long as the packaging form defines a constant amount, and includes containers capable of containing them such as wrapping papers, bags, soft bags, paper containers, cans, bottles and capsules.

The composition for promoting the production of BDNF and agent for promoting the production of BDNF according to the present invention are preferably continuously administered or fed for at least 2 weeks in order to exert the effect better, and the administration or feeding period is more preferably 2 to 8 weeks, especially preferably 4 to 8 weeks. The term "continuously" as used herein means continuation of daily administration or feeding. When the composition for promoting the production of BDNF and agent for promoting the production of BDNF according to the present invention are provided in a packaged form, an effective intake for a certain period (for example, 1 week) may be provided as a set for continuous feeding.

EXAMPLE

Hereinafter, the present invention will be described in detail by way of the following examples, but is not limited thereto.

Example 1

Study on BDNF Production Promoting Effect of Cacao Polyphenols

The following test was conducted in order to verify the influence of cacao polyphenols on the production of BDNF.

Three hundred and forty seven (347) adults being from 45 to 69 years old (123 males and 224 females) were used as subjects, and 25 g of a commercial cacao polyphenol-rich fat-processed composition ("Chocolate Koka Cacao 72%," Meiji Co., Ltd.) (5 tablets each containing 5 g of the fat-processed composition) was continuously fed to the subjects daily for four weeks. The above fat-processed composition contains 127 mg cacao polyphenols per tablet (total amount of polyphenols), and thus the amount of cacao polyphenols to be fed to the subjects daily is 635 mg.

The content of monomeric to tetrameric polyphenols to be fed daily, in the above fat-processed composition, was 76 mg. The main ingredients were: 10.4 mg of catechin (monomer), 27.8 mg of epicatechin (monomer), 15.8 mg of procyanidin B2 (dimer), 4.4 mg of procyanidin B5 (dimer), 9.6 mg of procyanidin C1 (trimer), and 7.1 mg of cinnamtannin A2 (tetramer). The respective ingredients were measured by using HPLC. The column used was Deverosil-ODS-HG5 (4.6 mm×250 mm, φ: 5µ, manufactured by Nomura Chemical Co., Ltd.). An eluent was composed of liquid A and liquid B, and an aqueous 0.1% trifluoroacetic acid solution and a 0.1% trifluoroacetic acid/acetonitrile solution were used as liquid A and liquid B, respectively. The flow rate of the eluent flowing through the column was 0.8 ml/min., and the conditions for gradient were as follows: the proportion of liquid B to the entire eluent was 10% at the initiation point, 10% 5 minutes after the initiation, 25% 35 minutes after the initiation, 100% 40 minutes after the initiation, and 100% 45 minutes after the initiation. The sample injection amount was 10 µL, and epicatechin was used as a reference standard to quantify the respective ingredients in terms of epicatechin equivalent. Also, the polyphenol content was measured by the Prussian blue method. Specifically, the polyphenol content was calculated by using commercial epicatechin as a standard substance according to the method described in Martin L. Price and Larry G. Butler, J. Agric Food Chem., Vol. 25, No. 6, 1268-1273, 1977.

The feeding initiation day was defined as Day 1, and blood sampling was conducted on the day before the feeding initiation day (Day 0) and the final feeding day (Day 28) to measure the BDNF protein concentration in serum. The BDNF protein concentration was measured by using an antibody chip (manufactured by Healthcare Systems) (n=2 per subject).

As for the obtained results, a Wilcoxon signed rank test was conducted on the BDNF protein concentration on Day 0 and the BDNF protein concentration on Day 28, and it was determined that there was a significant difference when the level of significance (p value) was less than 5%.

The results were as indicated in Table 1.

TABLE 1

BDNF concentration in serum before and after feeding

| | All subjects (n = 347) | | |
|---|---|---|---|
| Inspection item | Day 0 (average) | Day 28 (average) | p value |
| BDNF (ng/ml) | 6.07 ± 3.13 | 7.39 ± 5.87 | 0.005 |

From the results indicated in Table 1, it was confirmed that, upon feeding of cacao polyphenols, the BDNF protein concentration in serum significantly increased.

BDNF is associated with the control of mood, and it has been reported that the serum BDNF concentration decreases in patients with depression, but recovers when an antidepressant takes effect (Non-Patent Document 1). Then, subjects having a serum BDNF concentration before feeding (Day 0) at the first quartile or less (the BDNF concentration in serum was 4.38 ng/ml or less) were defined as subjects having a low initial value, and a Wilcoxon signed rank test was conducted in the same manner as described above.

The results were as indicated in Table 2.

TABLE 2

Results on subjects having BDNF concentration of first quartile or less

| | Subjects having BDNF concentration of first quartile or less | | |
|---|---|---|---|
| Inspection item | Day 0 (average) | Day 28 (average) | P value |
| BDNF (ng/ml) | 2.87 ± 0.95 | 6.92 ± 3.20 | <0.001 |

From the results indicated in Table 2, it was confirmed that, upon feeding of cacao polyphenols, the serum BDNF protein concentration significantly increased also in the subjects having a low initial value. Also, from the fact that the subjects having a low initial value showed a higher degree of increase than those of all the subjects, it was suggested that this increasing effect was more effective on the subjects having a low initial value. It is known that patients with depression or dementia have a low serum BDNF protein concentration, and that the improvement in disease conditions of these patients is correlated with the rise in serum BDNF protein concentration. Thus, the feeding of cacao polyphenols was demonstrated to be effective in improving depression, Alzheimer's dementia and the like.

From the above results, cacao polyphenols were confirmed to promote the production of BDNF, and the feeding of cacao polyphenols was demonstrated to have the effect of improving diseases and disease conditions which are improved by promoting the production of BDNF, such as depression.

The invention claimed is:

1. A method for promoting the production of a brain-derived neurotrophic factor (BDNF) comprising:
   measuring the serum BDNF concentration in an individual;
   administering to the individual an amount of cacao polyphenols effective to promote the production of BDNF in the individual daily for at least two weeks, wherein the individual has a serum BDNF concentration of 0.1 to 6 ng/ml prior to the administration of the cacao polyphenols; and wherein the amount of cacao polyphenols, which is effective in promoting the production of BDNF, ranges from 10 mg to 2,000 mg total amount of polyphenols.

2. The method for promoting the production of BDNF according to claim 1, wherein the cacao polyphenols are administered in the form of a fat-processed composition.

3. The method for promoting the production of BDNF according to claim 1, wherein the cacao polyphenols comprise 8% by mass or more of monomeric to tetrameric polyphenols.

4. A method for treating, preventing or improving a symptom of a disease that is effectively treated, prevented or improved by promoting the production of BDNF, which comprises:
measuring serum BDNF concentration in a subject; and
administering an effective amount of cacao polyphenols to the subject, wherein the subject has a serum BDNF concentration of 0.1 to 6 ng/ml prior to the administration of the cacao polyphenols, and a daily amount of cacao polyphenols which is effective in promoting the production of BDNF ranges from 10 mg to 2,000 mg total amount of polyphenols.

5. The method for promoting the production of BDNF according to claim 4, wherein the cacao polyphenols are administered in the form of a fat-processed composition.

6. The method according to claim 4, wherein the disease is a neurological disease.

7. The method according to claim 6, wherein the neurological disease is selected from the group consisting of depression, depressive state, schizophrenia, developmental disorder, and dementia.

8. The method according to claim 1, wherein the amount of cacao polyphenols administered to the individual per day ranges from 500 mg to 1,000 mg total amount of polyphenols.

9. The method according to claim 1, wherein the administration occurs for four weeks and increases serum BDNF in the individual by at least 100%.

10. The method according to claim 1, wherein the amount of cacao polyphenols administered to the individual is greater than 127 mg per day.

11. The method according to claim 1, wherein the serum concentration of BDNF following administration is 1.5 times greater than prior to administration.

12. The method according to claim 4, wherein the amount of cacao polyphenols administered to the subject per day ranges from 500 mg to 1,000 mg total amount of polyphenols.

13. The method according to claim 4, wherein the administration occurs for four weeks and increases serum BDNF in the subject by at least 100%.

14. The method according to claim 4, wherein the amount of cacao polyphenols administered to the subject is greater than 127 mg per day.

15. The method according to claim 4, wherein the serum concentration of BDNF following administration is 1.5 times greater than prior to administration.

* * * * *

UNITED STATES PATENT AND TRADEMARK OFFICE
CERTIFICATE OF CORRECTION

PATENT NO. : 10,695,317 B2
APPLICATION NO. : 15/572189
DATED : June 30, 2020
INVENTOR(S) : Midori Natsume et al.

Page 1 of 1

It is certified that error appears in the above-identified patent and that said Letters Patent is hereby corrected as shown below:

On the Title Page

Column 2, item [56], Line 24, delete "Kogak" and insert -- Kogaku --

Column 2, item [56], Line 40, delete "brian-derived" and insert -- brain-derived --

In the Claims

Column 11, Line 11, Claim 4, after "preventing" insert -- , --

Column 11, Line 12, Claim 4, after "prevented" insert -- , --

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*